(12) United States Patent
Shuey et al.

(10) Patent No.: US 11,903,831 B2
(45) Date of Patent: Feb. 20, 2024

(54) DEVICES, SYSTEMS, AND METHODS FOR ANCHORING AN ARTIFICIAL CHORDAE TENDINEAE TO A PAPILLARY MUSCLE OR HEART WALL

(71) Applicant: Boston Scientific Scimed, Inc., Maple Grove, MN (US)

(72) Inventors: Daniel Shuey, Pine City, MN (US); Joel T. Eggert, Plymouth, MN (US); Aaron Abbott, Columbia Heights, MN (US); James P. Rohl, Prescott, WI (US); Christopher J. Koudela, New London, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 48 days.

(21) Appl. No.: 16/919,794

(22) Filed: Jul. 2, 2020

(65) Prior Publication Data
US 2021/0000598 A1    Jan. 7, 2021

Related U.S. Application Data

(60) Provisional application No. 62/870,343, filed on Jul. 3, 2019.

(51) Int. Cl.
*A61F 2/24*    (2006.01)

(52) U.S. Cl.
CPC .......... *A61F 2/2457* (2013.01); *A61F 2/2466* (2013.01); *A61F 2210/0014* (2013.01);
(Continued)

(58) Field of Classification Search
CPC ........ A61B 17/0401; A61B 2017/0464; A61B 2017/00243; A61B 17/0644;
(Continued)

(56) References Cited

U.S. PATENT DOCUMENTS

| 7,736,388 B2 | 6/2010 | Goldfarb et al. |
| 8,252,050 B2 | 8/2012 | Maisano et al. |

(Continued)

OTHER PUBLICATIONS

International Search Report and Written Opinion for the International Patent Application No. PCT/US2020/040678, dated Oct. 16, 2020, 10 pages.

*Primary Examiner* — Matthew J Lawson
*Assistant Examiner* — Rebecca Lynee Zimmerman
(74) *Attorney, Agent, or Firm* — Seager, Tufte & Wickhem, LLP

(57) ABSTRACT

The present disclosure relates generally to the field of medical devices for delivering artificial chordae tendineae in a patient. In an embodiment, an anchor is movable between a delivery configuration and a deployed configuration, the anchor being in the delivery configuration when disposed within a delivery catheter, the anchor being in the deployed configuration when the anchor is moved beyond a distal end of the delivery catheter. When the anchor is in the delivery configuration it has a first outer dimension and when the anchor is in the deployed configuration it has a second outer dimension, the first outer dimension being smaller than the second outer dimension. The anchor is engageable with a papillary muscle or a heart wall when the anchor is in the deployed configuration and is also coupleable to an artificial chordae tendineae to anchor the artificial chordae tendineae to the papillary muscle or heart wall.

16 Claims, 9 Drawing Sheets

(52) U.S. Cl.
CPC ............... *A61F 2220/0008* (2013.01); *A61F 2220/0016* (2013.01)

(58) Field of Classification Search
CPC .... A61B 2017/0417; A61B 2017/0441; A61B 2017/0641; A61B 2017/0645; A61B 2017/0649; A61B 2017/00867; A61B 2017/0409; A61B 2017/0412; A61F 2/2457; A61F 2/2466; A61F 2210/0014; A61F 2220/0008; A61F 2220/0016
See application file for complete search history.

(56) References Cited

U.S. PATENT DOCUMENTS

| | | |
|---|---|---|
| 9,681,864 B1 | 6/2017 | Gammie et al. |
| 10,136,993 B1 | 11/2018 | Metchik et al. |
| 10,179,236 B2 | 1/2019 | Haasl et al. |
| 2004/0230280 A1 | 11/2004 | Cates et al. |
| 2006/0207607 A1 | 9/2006 | Hirotsuka et al. |
| 2007/0118151 A1 | 5/2007 | Davidson |
| 2008/0051863 A1 | 2/2008 | Schneider et al. |
| 2008/0195126 A1 | 8/2008 | Solem |
| 2009/0105729 A1 | 4/2009 | Zentgraf |
| 2011/0060407 A1 | 3/2011 | Ketai et al. |
| 2012/0172892 A1 | 7/2012 | Grubac et al. |
| 2013/0110230 A1* | 5/2013 | Solem ................... A61F 2/0077 623/2.38 |
| 2015/0250590 A1 | 9/2015 | Gries et al. |
| 2017/0245993 A1 | 8/2017 | Gross et al. |
| 2017/0252032 A1 | 9/2017 | Hiorth et al. |
| 2018/0185153 A1 | 7/2018 | Bishop et al. |
| 2018/0250133 A1 | 9/2018 | Reich et al. |
| 2018/0280685 A1* | 10/2018 | Toy ........................ A61N 1/056 |
| 2018/0296327 A1 | 10/2018 | Dixon et al. |
| 2018/0303614 A1 | 10/2018 | Schaffner et al. |
| 2020/0188115 A1* | 6/2020 | Dorff .................... A61F 2/2466 |

\* cited by examiner

DEVICES, SYSTEMS, AND METHODS FOR ANCHORING AN ARTIFICIAL CHORDAE TENDINEAE TO A PAPILLARY MUSCLE OR HEART WALL

CROSS-REFERENCE TO RELATED APPLICATIONS

The present application claims the benefit of priority under 35 U.S.C. § 119 to U.S. Provisional Patent Application 62/870,343, filed Jul. 3, 2019, which application is incorporated herein by reference in its entirety for all purposes.

FIELD

The present disclosure relates generally to the field of medical devices for anchoring to a heart wall. In particular, the present disclosure relates to medical devices, systems, and methods for delivering artificial chordae tendineae in a patient.

BACKGROUND

Mitral valve disease is typically repaired via invasive surgical intervention or by complicated pinching of the leaflets together creating dual, smaller openings, or a mitral valve replacement of the native valve. These approaches involve risky by-pass surgery that may include an opening into the patient's chest and heart chamber to expose the mitral valve for direct viewing and repair. Resection, partial removal, and/or repair of the patient's leaflets along with the implantation of a surgical ring are complex techniques used by surgeons to reduce the diameter of the patient's mitral annulus, thus allowing the leaflets to properly coapt and reduce mitral regurgitate flow. Some techniques may slightly reduce regurgitate flow but may not provide a durable solution and do not repair and/or replace damaged chordae tendineae of a valve. Thus, transluminal solutions to mitral valve disease are needed.

A variety of advantageous medical outcomes may be realized by the medical devices, systems, and methods of the present disclosure, which involve anchoring to a heart wall.

SUMMARY

Embodiments of the present disclosure may assist generally with clamping of a heart valve and providing a connection point for a filament. In one aspect, a system is disclosed for anchoring an artificial chordae tendineae to a papillary muscle or heart wall. The system may include an anchor movable between a delivery configuration and a deployed configuration. The anchor may be in the delivery configuration when disposed within a delivery catheter and may be in the deployed configuration when the anchor is moved beyond a distal end of the delivery catheter. When the anchor is in the delivery configuration the anchor can have a first outer dimension and when the anchor is in the deployed configuration the anchor can have a second outer dimension. The first outer dimension may be smaller than the second outer dimension. The anchor can be engageable with a papillary muscle or a heart wall when the anchor is in the deployed configuration. The anchor can be coupleable to the artificial chordae tendineae to anchor the artificial chordae tendineae to the papillary muscle or heart wall.

The anchor may have a plurality of arms coupled at a proximal end thereof to a body portion. At least one arm of the plurality of arms may be movable between a first position and a second position when the anchor moves from the delivery configuration to the deployed configuration. The plurality of arms can each having a distal tip for engaging the papillary muscle or heart wall. The distal tip of the at least one arm may be engageable with the papillary muscle or the heart wall when the at least one arm moves from the first position to the second position. In some embodiments all of the plurality of arms are movable between the first position and the second position.

The anchor can be movable from the delivery configuration and the deployed configuration as the anchor is expelled from a distal end of the delivery catheter. As the anchor is moved from the delivery and deployed configurations, the plurality of arms can move from an elongated shape to a curved shape. The plurality of arms can move from the first position to the second position due to a bias in each of the plurality of arms. In some non-limiting example embodiments, the plurality of arms are made from a shape memory material.

The at least one arm can be receivable through an opening in another one of said plurality of arms when the at least one arm moves from the first position to the second position. The at least one arm can have a curved shape so that in a neutral configuration in which no external forces are applied to the at least one arm, a central portion of the at least one arm is received within the opening. The at least one arm can form a loop for locking the anchor to the papillary muscle or the heart wall. In some embodiments the at least one arm is made from a shape memory material.

In some embodiments the anchor includes a braid portion. The anchor can also have an inner member extending through a body portion and the braid portion. The inner member may be coupled to a needle portion. The braid portion can be movable from the delivery configuration to the deployed configuration by moving the inner member with respect to one end of the braid portion.

A device is disclosed for anchoring to a papillary muscle or heart wall. The device may include an anchor movable between a delivery configuration and a deployed configuration. The anchor can be in the delivery configuration when disposed within a delivery catheter and can be in the deployed configuration when the anchor is moved beyond a distal end of the delivery catheter. When the anchor is in the delivery configuration the anchor has a first outer dimension and when the anchor is in the deployed configuration the anchor has a second outer dimension. The first outer dimension may be smaller than the second outer dimension. The anchor can engage a papillary muscle or heart wall when the anchor is in the deployed configuration. In some non-limiting example embodiments, the anchor comprises a braid portion.

The anchor may include a body portion and a plurality of arms coupled at a proximal end thereof to the body portion. At least one arm of the plurality of arms can be movable between a first position and a second position when the anchor moves from the delivery configuration to the deployed configuration. The plurality of arms can each have a distal tip for engaging the papillary muscle or heart wall. In some embodiments all of the plurality of arms are movable between the first position and the second position.

In some embodiments the at least one arm is receivable through an opening in another one of the plurality of arms when the at least one arm moves from the first position to the second position. The anchor may be movable between the delivery configuration and the deployed configuration as the anchor is expelled from a distal end of the delivery catheter.

As the anchor is moved between the delivery and deployed configurations, the plurality of arms can move from an elongated shape to a curved shape.

A method is disclosed for anchoring an artificial chordae tendineae to a papillary muscle or heart wall. The method may include: inserting a catheter through a heart valve, the catheter containing an anchor having a body portion coupled to an artificial chordae tendineae, positioning the catheter adjacent to a targeted papillary muscle or heart wall, and moving the anchor out of the catheter so that the anchor moves from a delivery configuration to a deployed configuration. When the anchor is in the delivery configuration the anchor has a first outer dimension and when the anchor is in the deployed configuration the anchor has a second outer dimension. The first outer dimension being smaller than the second outer dimension. The anchor may be engaged with the targeted papillary muscle or heart wall when the anchor is moved to the deployed configuration. The method may also include visualizing, using a medical visualization technique, the position of the anchor with respect to the targeted papillary muscle or heart wall before moving the anchor out of the catheter. The anchor further having at least one arm coupled to the body portion, the at least one arm moving from a first position to a second position when the anchor is moved from the delivery configuration to the deployed configuration. When the arm of the anchor moves from the first position to the second position a tip of the arm pierces the targeted papillary muscle or heart wall. The anchor may have a plurality of arms coupled to the body portion. When the anchor is moved out of the catheter the plurality of arms can move from a first position to a second position to engage the targeted papillary muscle or heart wall.

BRIEF DESCRIPTION OF THE DRAWINGS

Non-limiting embodiments of the present disclosure are described by way of examples with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
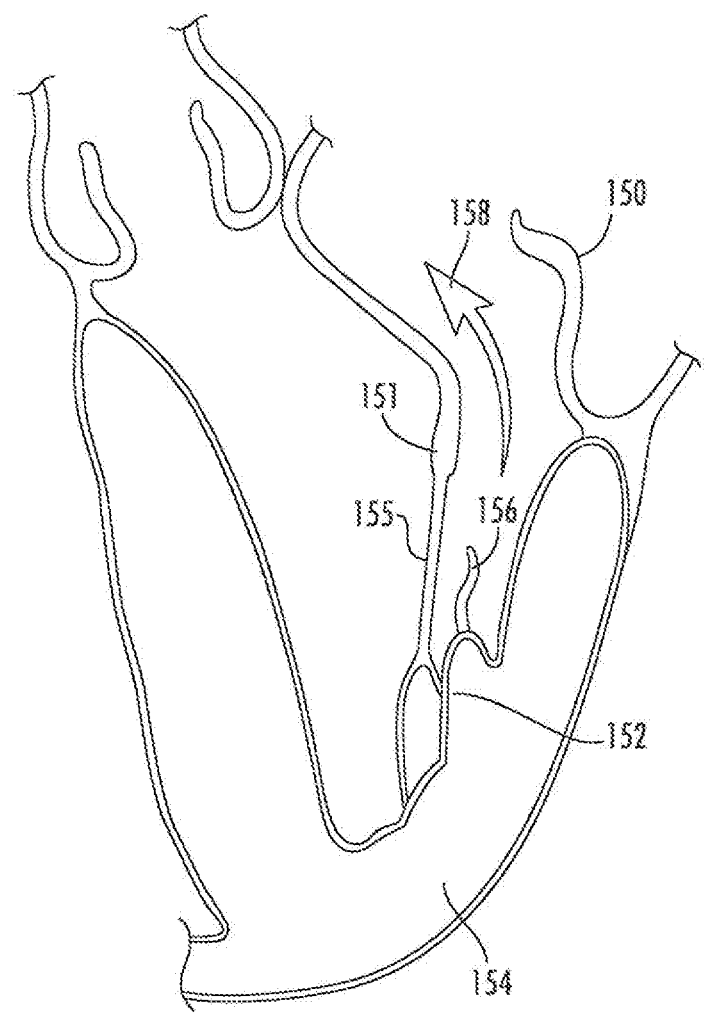
FIG. 1 illustrates a cross-sectional view of flailing leaflet of a mitral valve during blood flow regurgitation.

The present disclosure is not limited to the particular embodiments described. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures that require anchoring to hear tissue. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components and/or groups thereof.

As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment," "some embodiments," "other embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

Heart disease including atrioventricular heart valve malfunctions impede patient cardiac output, which reduces patient quality of life and lifespan. With reference to the heart 154 illustrated in FIG. 1, as heart disease progresses, the chordae tendineae 155 that connect the papillary muscle or heart wall 152 to a valve leaflet 151 may stretch inelastically and may rupture. A stretched and/or ruptured chordae tendineae 156 may result in a flailing leaflet 150 that may no longer have capacity to form a valving seal for normal heart function. For example, abnormal blood flow regurgitation in the direction of vector 158 may develop. Regurgitation prevents an adequate supply of blood to be delivered through the cardiovascular systems.

Repositioning, repair, and/or replacement of one or more leaflets of a valve and/or chordae tendinea may be used to treat heart disease. The devices, systems, and methods of the present disclosure may be used alone or together with other devices, systems, and methods to treat heart disease. Examples of devices, systems, and methods with which embodiments of the present disclosure may be implemented include, but are not limited to, those described in U.S. Patent Application Publication No. 2021/0000597, filed Jul. 2, 2020, and titled DEVICES, SYSTEMS, AND METHODS FOR ADJUSTABLY TENSIONING AN ARTIFICIAL CHORDAE TENDINEAE BETWEEN A LEAFLET AND A PAPILLARY MUSCLE OR HEART WALL; U.S. Patent Application Publication No. 2021/0007847, filed Jul. 2, 2020, and titled DEVICES, SYSTEMS, AND METHODS FOR CLAMPING A LEAFLET OF A HEART VALVE; and U.S. Patent Application Publication No. 2021/0000599, filed Jul. 2, 2020, and titled DEVICES, SYSTEMS, AND METHODS FOR ARTIFICIAL CHORDAE TENDINEAE, each of which is herein incorporated by reference in its entirety and for all purposes. Examples of devices described therein may be modified to incorporate embodiments or one or more features of the present disclosure.

Repositioning, repair, and/or replacement of one or more leaflets of a valve and/or chordae tendinea may require one or more devices to be fixed to a portion of a heart wall. Embodiment devices described herein may be fixed to a heart wall by engaging an anchor with the papillary muscle and/or the heart wall. Such devices may provide a fixed point for other devices, systems, or tools to engage in order to manipulate a leaflet of a valve and/or to deliver devices attached to the papillary muscle and/or heart wall.

It will be appreciated that one or more aspects of the disclosed anchors may be delivered to a papillary muscle and/or heart wall using a catheter or other appropriate delivery device. For example, a catheter may be used to move one or more of the disclosed anchors from a delivery configuration (e.g., when the anchor is disposed within a portion of the catheter) to a deployed configuration (e.g., where the anchor is dispensed beyond an end portion of the catheter so that it can engage the papillary muscle and/or heart wall at a targeted location). The catheter may have one or more controls to enable a user to dispense an anchor from the catheter, such as by manipulating one or more cables, wires or the like. In some embodiments, the catheter may also have one or more controls to enable a user to rotate an anchor before, during or after the anchor is dispensed from the catheter to facilitate engagement of the anchor with targeted tissue.

As will be appreciated, the specific nature of the delivery device is not critical to the present disclosure, as long as the delivery device is configured to allow a user to deliver and implant the anchor at a targeted heart tissue location.

It will also be appreciated that delivery, deployment, and engagement of the disclosed embodiments may be facilitated by use of known medical visualization techniques, such as fluoroscopy, ultrasound, intra-cardiac echo, or the like.

With reference now to FIGS. 2A-2D, embodiments of an anchor 200 for engaging a targeted papillary muscle or heart wall according to the present disclosure are illustrated. In general, the anchor 200 may have a plurality of arms 202*a-c* having proximal ends 204*a-c* coupled to a body portion 206, and distal ends 208*a-c* that extend away from the proximal ends. The distal ends 208*a-c* may each have a tapered or pointed tip 210*a-c* suitable for piercing tissue so that the anchor 200 may be securely fixed to a targeted tissue site when the anchor is engaged therewith.

The arms 202*a-c* may have a bowed appearance such that when the arms are in a neutral position (e.g., not acted upon by an outside force) a central portion 211*a-c* of each of the arms extends radially outwardly from the body portion 206 by a distance greater than a distance between the body portion and the distal ends 208*a-c* of the arms. In addition, the pointed tips 210*a-c* of each of the arms 202*a-c* may point away from the body portion 206 when the arms are in the aforementioned neutral position.

Figure 2A:
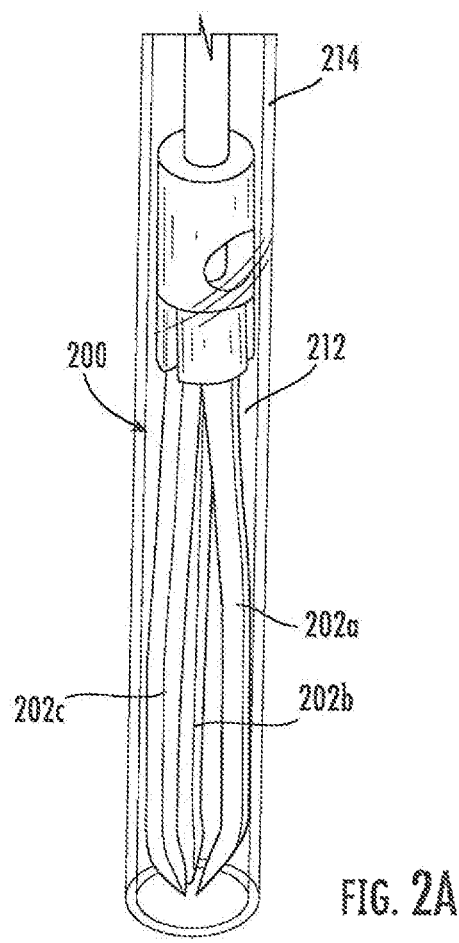
FIG. 2A illustrates a perspective view of an anchor in a delivery configuration according to an embodiment of the present disclosure.
Figure 2B:
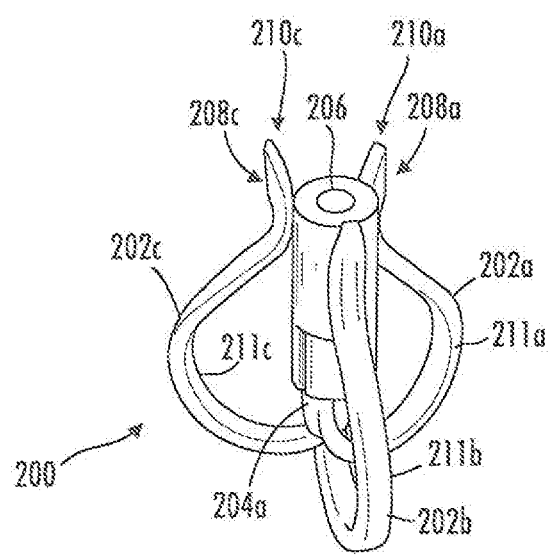
FIG. 2B illustrates a perspective view of the anchor of FIG. 2A in a deployed configuration.

FIG. 2A shows the plurality of arms 202*a-c* positioned in a configuration (referred to as a delivery configuration) that enables the anchor 200 to be contained within the lumen 212 of an appropriate catheter 214 or other delivery device. In this configuration, the anchor 200 may be carried, via the catheter, to a targeted tissue site where it can then be deployed for engagement with targeted papillary muscle or heart wall. In the delivery configuration the plurality of arms 202*a-c* may be pressed together, with the result being that the plurality of arms assume an elongated, somewhat flattened, shape. In some embodiments the plurality of arms 202a-c are made from a material that has an elastic characteristic that enable the arms to be pressed toward each other to assume the delivery configuration. In one embodiment the plurality of arms 202a-c are made from a shape memory material such as Nitinol. Thus arranged, when the plurality of arms 202a-c are positioned in the delivery configuration they may be biased away from each other. When the anchor 200 is disposed within the lumen 212 of the catheter 214, the plurality of arms 202a-c are maintained in the delivery configuration of FIG. 2A. When the anchor 200 is moved out of the lumen 212 of the catheter 214, the bias in the plurality of arms 202a-c causes them to move away from each other to assume the deployed configuration shown in FIG. 2B. In moving from the delivery configuration to the deployed configuration, the plurality of arms 202a-c move outward so that the tips 210a-c of the arms engage and penetrate the targeted papillary muscle or heart wall. In some embodiments the tips 210a-c pierce the papillary muscle or heart wall so that the muscle or heart wall is held firmly by the central portions 211a-c of the plurality of arms 202a-c.

Figure 2C:
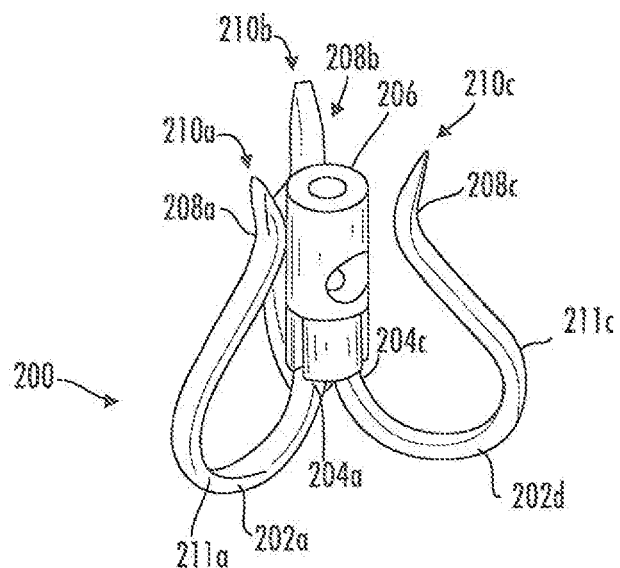
FIG. 2C illustrates an alternative arm configuration for the anchor of FIGS. 2A and 2B.
Figure 2D:
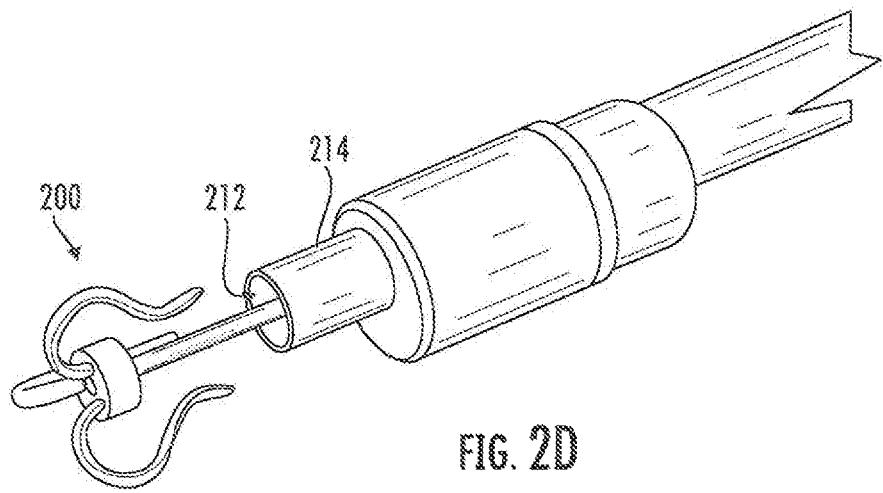
FIG. 2D illustrates the anchor of FIGS. 2A and 2B coupled to a deployment wire and adjacent an end of an example delivery catheter.

FIG. 2C illustrates an embodiment of an anchor 200 in which the plurality of arms 202a-c can cross each other as they move from the delivery configuration to the deployed configuration. As can be seen, the proximal ends 204a-c of the plurality of arms 202a-c are coupled to the body portion 206 on opposite sides of the body portion as compared to the connection arrangement illustrated in the embodiment of FIG. 2B. By forming and positioning the plurality of arms 202a-c in this manner, upon deployment the arms can form loops with which to trap tissue as they deploy.

As can be seen, the anchor embodiments illustrated in FIGS. 2A-2D includes arms 202a-c that are biased so that in the deployed configuration the distal ends 208a-c of the arms are directed inward toward the body portion 206. In the illustrated embodiment, the arms 202a-c are disposed at substantially 120-degree intervals, though this is not critical and other angular spacings of the arms can also be used without departing from the scope of the disclosure. In addition, it will be appreciated that although the anchor 200 is shown as including three arms 202a-c, the anchor 200 can have greater or fewer numbers of arms as desired.

Thus arranged, the anchor 200 has a delivery configuration, in which the anchor is disposed within the catheter 214, and a deployed configuration, in which the anchor is deployed outside the catheter. When the anchor 200 is in the delivery configuration, the arms 202a-c are in a first position. When the anchor 200 is deployed outside the catheter 214 the arms may move from the first position to a second position. Thus, the anchor 200 moves from a radially constrained configuration when disposed inside the catheter, to a radially expanded configuration when moved beyond the distal end of the catheter. In some embodiments the anchor 200 has a first outer dimension in the radially constrained configuration, and a second outer dimension in the radially expanded configuration. In some embodiments the first outer dimension is smaller than the second outer dimension.

With reference to FIGS. 3A-3D, an embodiment of an anchor 300 for engaging a targeted papillary muscle or heart wall according to the present disclosure is illustrated. The anchor 300 may have a plurality of arms 302a-c having proximal ends 304a-c coupled to a body portion 306, and distal ends 308a-c that extend away from the proximal ends. The distal ends 308a-c may each have a tapered or pointed tip 310a-c suitable for piercing tissue so that the anchor 300 may be securely fixed to a targeted tissue site when the anchor is engaged therewith.

Figure 3A:
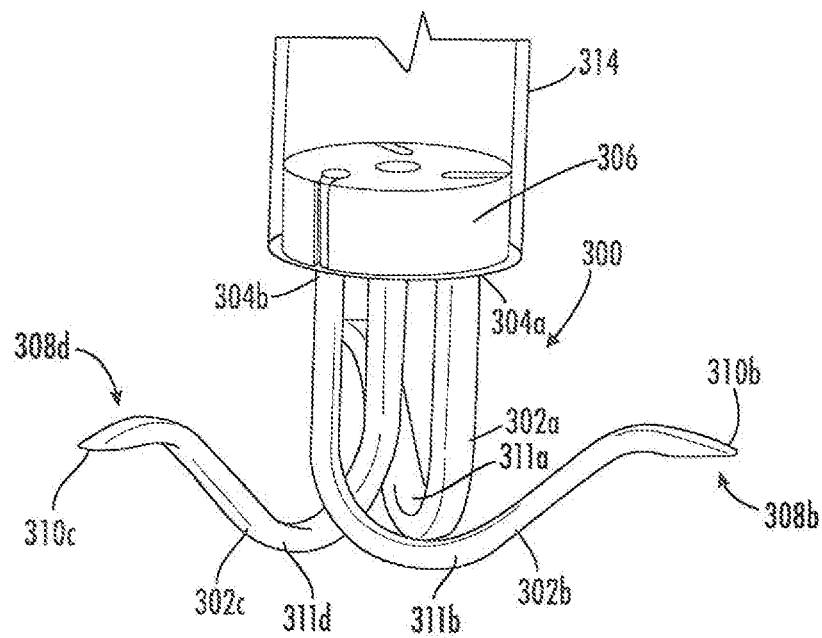
FIG. 3A illustrates a perspective view of an anchor in a deployed configuration according to an embodiment of the present disclosure.
Figure 3B:
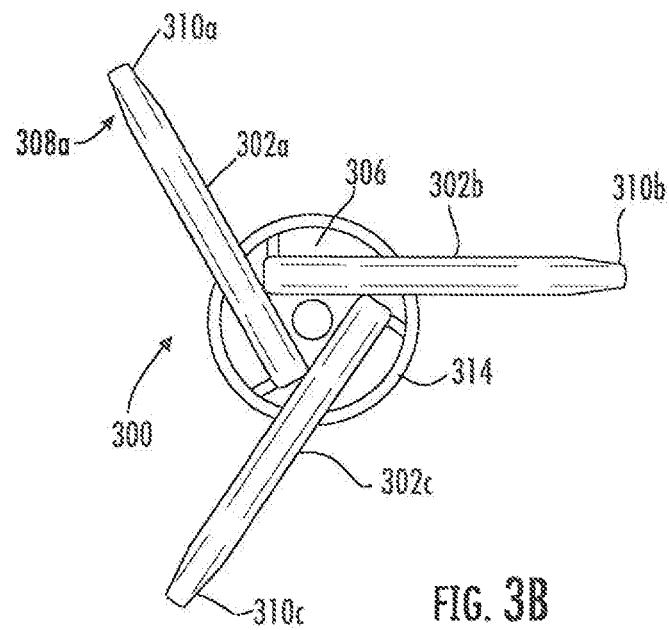
FIG. 3B illustrates a bottom view of the anchor of FIG. 3A.
Figure 3C:
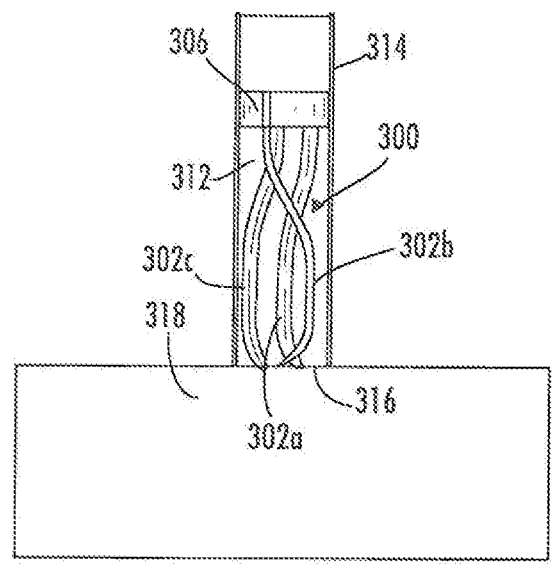
FIG. 3C illustrates a transparent side view of the anchor of FIGS. 3A and 3B in the delivery configuration, disposed within an example delivery catheter.
Figure 3D:
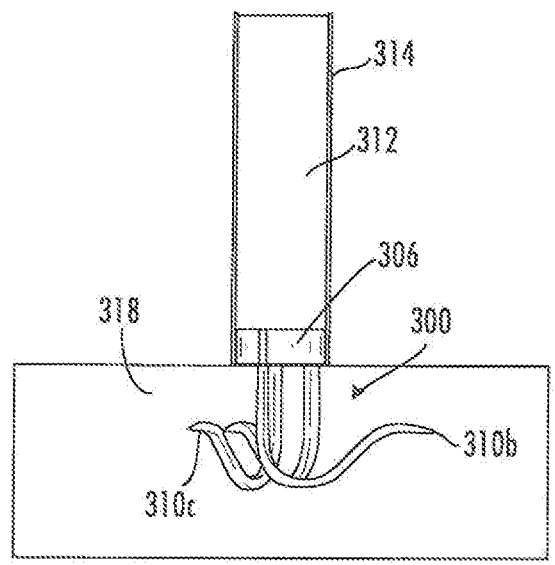
FIG. 3D illustrates a transparent side view of the anchor of FIG. 3A in the deployed configuration, disposed beyond an end of the delivery catheter.

FIG. 3C shows the plurality of arms 302a-c positioned in a delivery configuration within the lumen 312 of an appropriate catheter 314 or other delivery device. In this configuration, the anchor 300 may be carried, via the catheter 314, to a targeted tissue site where it can then be deployed. As can be seen, in the delivery configuration the plurality of arms 302a-c assume an elongated shape with the tips 310a-c pointing toward an open end 316 of the catheter 314. In some embodiments the plurality of arms 302a-c are made from a material that has an elastic characteristic that enable the arms to be pressed toward each other to assume the delivery configuration. In one embodiment the plurality of arms 302a-c are made from a shape memory material such as Nitinol. When the plurality of arms 302a-c are positioned in the delivery configuration they may be naturally biased away from each other. As will be appreciated, the catheter 314 may maintain the plurality of arms 302a-c in the delivery configuration until the anchor 300 is disposed adjacent to a targeted papillary muscle or heart wall 318. The anchor 300 may then be moved out of the lumen 312 of the catheter 314, whereupon the bias in the plurality of arms 302a-c may cause the arms to move away from each other to assume the deployed configuration shown in FIGS. 3A, B and D. When the arms 302a-c move from the delivery configuration to the deployed configuration, the plurality of arms 302a-c move apart so that the tips 310a-c of the arms engage and penetrate the targeted papillary muscle or heart wall 318, thus fixing the anchor 300 thereto.

As with the previous embodiment, the arms 302a-c of the illustrated anchor 300 may have a bowed appearance when the arms are in a neutral position (e.g., not acted upon by an outside force). A bowed central portion 311a-c of each of the arms 302a-c acts as a spring to move the tips 310a-c of the arms radially outwardly away from the body portion 306 when the anchor 300 is moved from the delivery configuration (within the catheter 314—FIG. 3C) to the deployed configuration (outside the catheter—FIG. 3D). Thus, in the deployed configuration of FIG. 3A, 3D, the pointed tips 310a-c of each of the arms 302a-c may point away from the body portion 306 to engage tissue.

As can be seen, the anchor 300 illustrated in FIGS. 3A-3D includes arms 302a-c that are biased so that in the deployed configuration the tips 310a-c point away from each other at substantially 120-degree intervals, though this is not critical and other angular spacings of the arms can also be used without departing from the scope of the disclosure. In addition, it will be appreciated that although the anchor 300 is shown as including three arms 302a-c, the anchor 300 can have greater or fewer numbers of arms as desired.

Thus arranged, the anchor 300 has a delivery configuration, in which the anchor is disposed within the catheter 314, and a deployed configuration, in which the anchor is deployed outside the catheter. When the anchor 300 is in the delivery configuration, the arms 302a-c are in a first position. When the anchor 300 is deployed outside the catheter 314 the arms may move from the first position to a second position. Thus, the anchor 300 moves from a radially constrained configuration when disposed inside the catheter, to a radially expanded configuration when moved beyond the distal end of the catheter. In some embodiments the anchor 300 has a first outer dimension in the radially constrained configuration, and a second outer dimension in the radially expanded configuration. In some embodiments the first outer dimension is smaller than the second outer dimension.

Figure 4A:
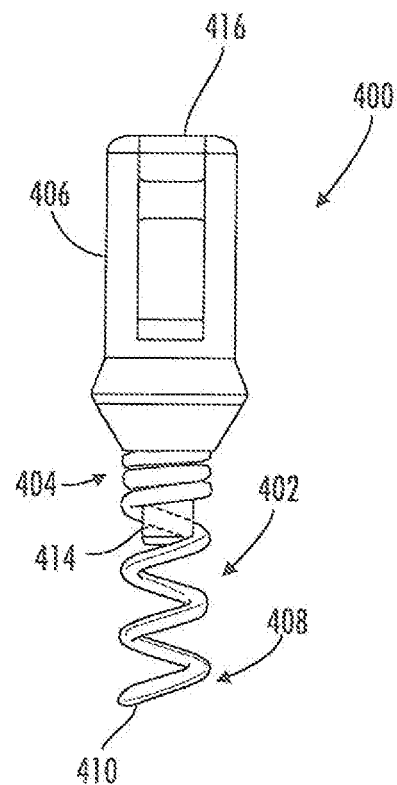
FIG. 4A illustrates a side view of an anchor according to an embodiment of the present disclosure
Figure 4B:
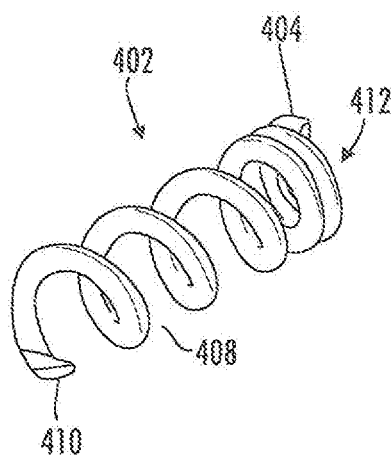
FIG. 4B illustrates a perspective view of a tissue engaging portion of the anchor of FIG. 4A.

FIGS. 4A-4B show an embodiment of an anchor 400 for engaging a papillary muscle or heart wall according to the present disclosure. The anchor 400 can include a tissue-engaging portion 402 having a proximal end 404 for engaging a body portion 406, and a distal end 408 extending away from the proximal end. The distal end 408 may have a tapered or pointed tip 410 suitable for piercing tissue so that the anchor 400 may be securely engaged with a targeted tissue site (papillary muscle or heart wall) when the anchor is coupled therewith.

As can be seen, in the illustrated embodiment the tissue-engaging portion 402 includes a wire-body formed in the shape of a helix. The proximal end 404 of the tissue-engaging portion may be an extension of the wire-body and may form an opening 412 for receiving a projection portion 414 of the body portion 406 therein to fix the body portion 406 to the tissue-engaging portion 402. In this manner the body portion 406 and the tissue-engaging portion 402 are rotationally and axially locked together.

In use, the targeted tissue can be engaged by piercing the tissue (e.g., papillary muscle or heart wall) with the tip 410 of the anchor 400 followed by rotation of the anchor via the body portion 406, which serves to draw the wire body of the tissue-engaging portion 402 down into deep engagement with the tissue.

Although not shown, the anchor 400 can be delivered to a papillary muscle or heart wall using a catheter or other appropriate delivery device. The body portion 406 can be coupled at one end 416 to a cable, wire, or the like so that axial and rotational forces can be applied to the anchor 400. For example, an axial force may be applied to move the anchor 400 out of the catheter by a sufficient amount to engage the tip 410 of the tissue-engaging portion 402 with a segment of the targeted papillary muscle or heart wall. Rotational force may then be applied to the anchor 400 so that the helix shape of the tissue-engaging portion 402 can act to draw the anchor into engagement with the papillary much or heart wall.

With reference to FIGS. 5A-5D, an embodiment of an anchor for engaging a targeted papillary muscle or heart wall according to the present disclosure is illustrated. The anchor 500 may have first and second arms 502, 504 and a body portion 506. The first and second arms 502, 504 may have respective distal tips 508, 510 which may be tapered or pointed to allow them to pierce tissue. The first and second arms 502, 504 may also include proximal ends 512, 514 that are coupled to, or formed integrally with, the body portion 506.

The first arm 502 may further include an opening 516 positioned between the distal tip 508 and the proximal end 514 of the second arm 504. The opening 516 may be sized to receive the distal tip 510 of the second arm 504 therethrough when anchor 500 is moved between the delivery and deployed configurations.

Figures 5A, 5B:
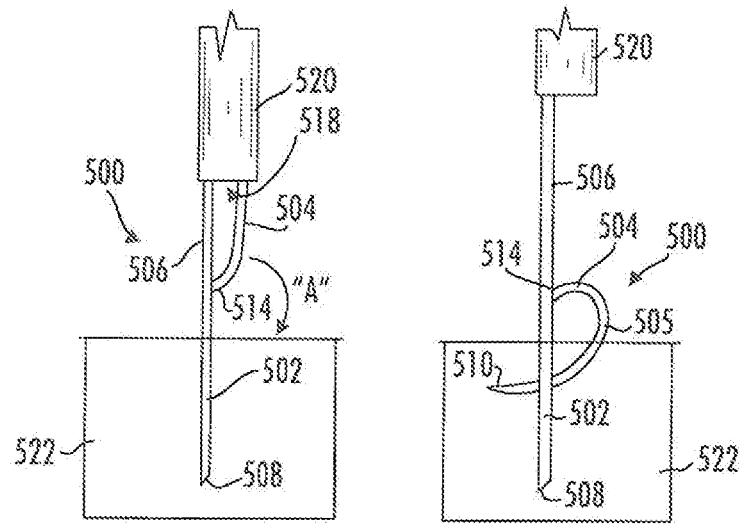
FIG. 5A illustrates a side view of an anchor in a delivery configuration, according to an embodiment of the present disclosure.
FIG. 5B illustrates a side view of the anchor of FIG. 5A in a deployed configuration.
Figure 5C:
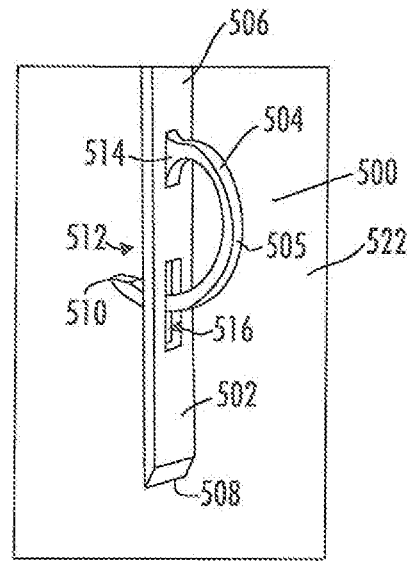
FIG. 5C illustrates a perspective view of the anchor of FIG. 5B.

FIG. 5A shows the anchor 500 in the partially deployed configuration. As can be seen, the second arm 504 remains in the delivery configuration (e.g., a portion thereof is positioned within the lumen 518 of a catheter 520). In this position the first arm 502 is deployed such that its distal tip 508 is engaged with targeted papillary muscle or heart wall 522. As the anchor 500 is moved further outward from the catheter 520 the second arm 504 is released, causing the second arm to rotate in the direction of arrow "A" to assume the deployed configuration shown in FIGS. 5B and 5C.

The second arm 504 may have a curved shape so that in a neutral configuration (e.g., when no external forces are applied to the second arm) a central portion 505 of the second arm is partially received within the opening 516 in the first arm 502. In this position (FIGS. 5B, 5C), the distal tip 510 is positioned beyond the opening 516 in the first arm 502 and is oriented at an oblique angle with respect to the first arm 502.

As the second arm 504 moves from the delivery configuration (FIG. 5A) to the deployed configuration (FIGS. 5B-C), the distal tip 510 moves in the direction of arrow "A" to puncture the targeted papillary muscle or heart wall 522. The distal tip 510 then moves within the tissue until it passes through the opening 516 in the first arm 502 and assumes the final position shown in FIGS. 5B and 5C. The anchor 500 is thus locked to the targeted papillary muscle or heart wall 522.

In some embodiments the second arm 504 is made from a material that has an elastic characteristic that causes it to move from the delivery configuration to the deployed configuration. In one embodiment the second arm 504 is made from a shape memory material such as Nitinol. Thus, when the second arm 504 is positioned in the delivery configuration it may be naturally biased outward. In the illustrated embodiment, the second arm 504 is bent so that its distal tip 510 is oriented in a direction opposite the distal tip 508 of the first arm 502. As will be appreciated, the catheter 520 may maintain the second arm 504 in the delivery configuration until the anchor 500 is disposed adjacent to a targeted papillary muscle or heart wall 522. The anchor 500 may then be moved out of the lumen 518 of the catheter 520 such that the distal tip 508 of the first arm 502 engages the papillary muscle or heart wall 522. The anchor 500 may be pressed further down into the papillary muscle or heart wall 522 until the second arm 504 is released from the catheter 520, whereupon the bias in the second arm may cause the second arm to assume the deployed configuration of FIGS. 5B and 5C.

Thus arranged, the anchor 500 has a delivery configuration, in which the anchor is disposed within the catheter 520, and a deployed configuration, in which the anchor is deployed outside the catheter. When the anchor 500 is in the delivery configuration, the second arm 504 is in a first position. When the anchor 500 is deployed outside the catheter 520 the second arm 504 may move from the first position to a second position. Thus, the anchor 500 can move from a radially constrained configuration when disposed inside the catheter 520 to a radially expanded configuration when moved beyond the distal end of the catheter. In some embodiments the anchor 500 has a first outer dimension in the radially constrained configuration, and a second outer dimension in the radially expanded configuration. In some embodiments the first outer dimension is smaller than the second outer dimension.

Figures 6A, 6B:
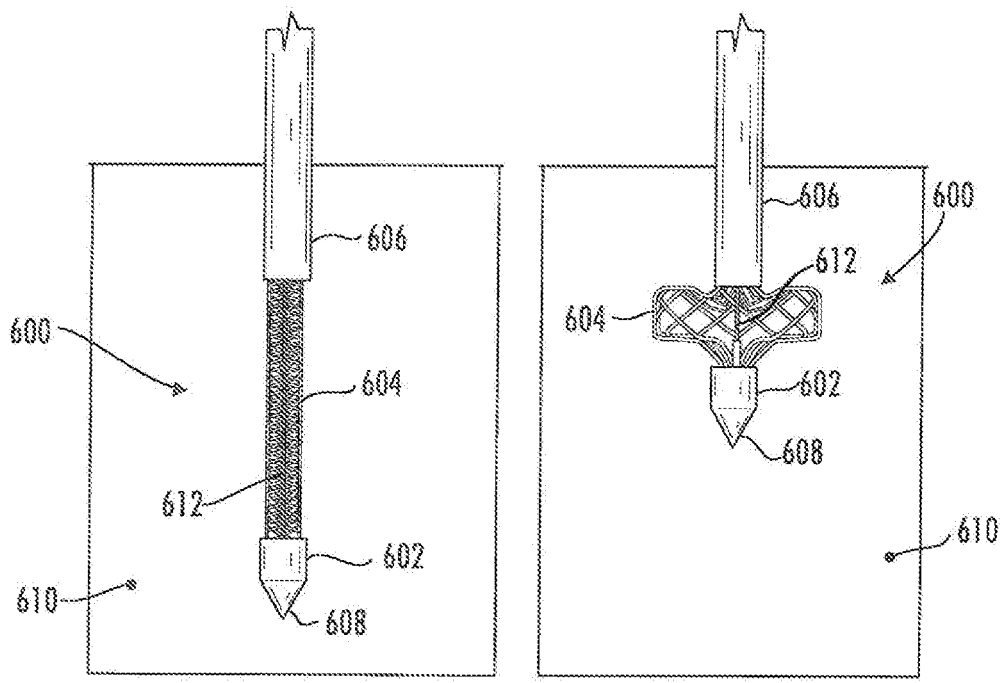
FIG. 6A illustrates a perspective view of an anchor in a delivery configuration, according to an embodiment of the present disclosure.
FIG. 6B illustrates a side view of the clamp of FIG. 6A in a deployed configuration.

With reference to FIGS. 6A-6B, an embodiment of an anchor for engaging a targeted papillary muscle or heart wall according to the present disclosure is illustrated. The anchor 600 may include a needle portion 602, a braid portion 604, and a body portion 606. The needle portion 602 may have a pointed end 608 to allow the needle portion to pierce the targeted papillary muscle or heart wall 610. An inner member 612 such as a wire, cable, coil or the like may extend through the body portion and the braid portion 604 and may be fixed to the needle portion 602. The inner member 612 may provide stiffness to the anchor during delivery and may be used to press the needle portion 602 into engagement with the targeted papillary muscle or heart wall 610.

The anchor 600 may be made from a flexible material, such as a shape memory material, so that the anchor may be deliverable in a radially compressed state and then can be radially expanded to assume the shape shown in FIG. 6B. In some embodiments the braid portion 604 may be formed of a flexible braided Nitinol or other appropriate material so that it can be selectively expanded. The braid portion 604 may be coupled to the needle portion 602 and the body portion 606 by welding, adhesive or other appropriate bonding technique.

As shown in FIG. 6A, the anchor 600 may be provided in a delivery configuration (e.g., a radially compressed state) for delivery to a targeted tissue site using an appropriate catheter. Once the anchor 600 is positioned at the targeted tissue site, the pointed end 608 of the needle portion 602 may be pressed into the tissue until the anchor is embedded within the tissue in a manner shown in FIG. 6A. The inner member 612 may then be retracted, which may expand the braid portion 604 so that it assumes the deployed configuration of FIG. 6B.

Thus arranged, the anchor 600 has a delivery configuration, in which the anchor is disposed within the delivery catheter (not shown), and a deployed configuration, in which the anchor is deployed outside the catheter. When the anchor 600 is in the delivery configuration, the braid portion 604 is in a first position. When the anchor 600 is deployed outside the delivery catheter the braid portion may move from the first position to a second position. Thus, the anchor 600 can move from a radially constrained configuration when disposed inside the catheter to a radially expanded configuration when moved beyond the distal end of the catheter. In some embodiments the anchor 600 has a first outer dimension in the radially constrained configuration, and a second outer dimension in the radially expanded configuration. In some embodiments the first outer dimension is smaller than the second outer dimension.

Figure 7:
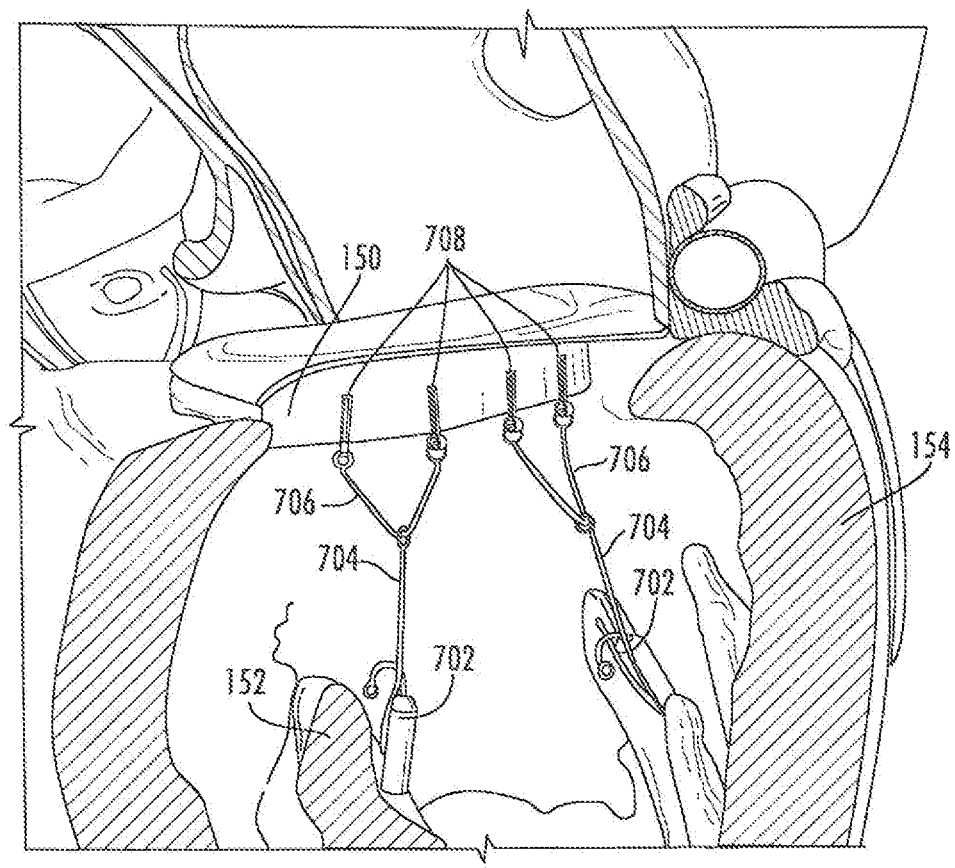
FIG. 7 illustrates a cross-sectional view of a system for engaging an anchor with a portion of a heart wall, according to an embodiment of the present disclosure.

With reference to FIG. 7, an embodiment system for anchoring to a papillary muscle or heart wall 152 according to the present disclosure is illustrated, including anchors 702 attached to the papillary muscle or heart wall 152 of a heart 154 Each of the anchors 702 is attached to an end of an anchoring filament 704 that is an artificial chordae tendineae. The anchoring filaments 704 are attached to a filament 706 that is further attached a plurality of leaflet clips 708 that are coupled to a leaflet 150 of a heart valve. A medical professional may adjust the length and tension of the filaments 706 and anchoring filaments 704 such that they may replicate and/or replace chordae tendineae of the heart 154 for function with the leaflet 150 of the valve. The medical professional may adjust filaments 704, 706 in response to a heart valve regurgitation observation that may be observed via transesophageal echocardiogram and/or fluoroscopy. The filaments 704, 706 are fixed at one end to the leaflet 150 by the clip(s) 708 and are fixed at a second end to the papillary muscle or heart wall 152 by the anchor(s) 702. A single anchoring filament 704 may be coupled to one or more filaments 706 such that one anchoring filament 704 and one anchor 702 may be used for multiple clips 708. In some embodiments, the filaments 706 and anchoring filaments 704 may be coupled to one or more clips 708 and to each other during delivery of the system into the heart 154.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for anchoring an artificial chordae tendineae to papillary muscle or heart wall, the system comprising:
   an anchor movable between a delivery configuration and a deployed configuration, the anchor being in the delivery configuration when disposed within a delivery catheter, the anchor being in the deployed configuration when the anchor is moved beyond a distal end of the delivery catheter;
   wherein:
   the anchor has a body portion and a tissue-engaging portion extending from the body portion;
   in the delivery configuration, the tissue-engaging portion of the anchor is elongated and extends axially away from the body portion with a distal tip thereof directed radially-inwardly;
   in the deployed configuration, the tissue-engaging portion of the anchor has a central portion extending radially away from the body portion of the anchor, a distal end extending radially and axially toward the body portion of the anchor, and a distal tip extending axially toward and radially away from the body portion of the anchor;
   when the anchor is in the delivery configuration the anchor has a first outer dimension, and when the anchor is in the deployed configuration the anchor has a second outer dimension, the first outer dimension being smaller than the second outer dimension;
   the tissue-engaging portion of the anchor is engageable with a papillary muscle or a heart wall when the anchor is in the deployed configuration, and
   the body portion of the anchor is configured to be coupled with the artificial chordae tendineae to anchor the artificial chordae tendineae to the papillary muscle or heart wall.

2. The system of claim 1, wherein the tissue-engaging portion of the anchor comprises a plurality of arms coupled to the body portion of the anchor, at least one arm of the plurality of arms having a proximal end coupled to the body portion, a distal end extending away from the proximal end of the arm, and a central portion between the proximal end and the distal end of the arm, the at least one arm being movable between a first elongated configuration and a second bowed configuration with the central portion of the arm extending radially away from the body portion of the anchor a greater distance than the distance between the distal end of the at least one of the plurality arms and the body portion of the anchor when the anchor moves from the delivery configuration to the deployed configuration.

3. The system of claim 1, wherein the tissue-engaging portion of the anchor comprises a plurality of arms coupled to the body portion of the anchor, at least one of the plurality of arms having a proximal end coupled to the body portion, and a pointed distal tip engageable with the papillary muscle or the heart wall and pointing axially toward the body portion and radially away from the body portion of the anchor when the anchor is in the deployed configuration.

4. The system of claim 2, wherein each of the plurality of arms has a proximal end coupled to the body portion, a distal end extending away from the proximal end of the arm, and a central portion between the proximal end and the distal end, and is movable between a first elongated configuration, and a second bowed configuration with the central portion of the arm extending radially away from the body portion of the anchor a greater distance than the distance between the distal end of the at least one of the plurality arms and the body portion of the anchor when the anchor moves from the delivery configuration to the deployed configuration.

5. The system of claim 2, wherein the anchor is movable between the delivery configuration and the deployed configuration as the anchor is expelled from a distal end of the delivery catheter.

6. The system of claim 4, wherein each of the plurality of arms has a distal tip extending axially toward the body portion of the anchor and pointing radially away from the body portion of the anchor when the arms are in the second bowed configuration.

7. The system of claim 1, wherein:
the tissue-engaging portion of the anchor comprises a plurality of arms coupled to the body portion of the anchor; and
the plurality of arms cross each other as they move from the first configuration to the second configuration.

8. A device for anchoring to a papillary muscle or heart wall, the device comprising:
an anchor movable between a delivery configuration and a deployed configuration, the anchor being in the delivery configuration when disposed within a delivery catheter, the anchor being in the deployed configuration when the anchor is moved beyond a distal end of the delivery catheter;
wherein:
the anchor has a body portion and a tissue-engaging portion extending from the body portion;
in the delivery configuration, the tissue-engaging portion of the anchor is elongated and extends axially away from the body portion with a distal tip thereof directed radially-inwardly;
in the deployed configuration, the tissue-engaging portion has a central portion extending radially away from the body portion of the anchor, a distal end extending-radially toward the body portion of the anchor and axially toward the body portion of the anchor, and a distal tip extending axially toward the body portion of the anchor and radially away from the body portion of the anchor;
when the anchor is in the delivery configuration the anchor has a first outer dimension and when the anchor is in the deployed configuration the anchor has a second outer dimension, the first outer dimension being smaller than the second outer dimension;
the tissue-engaging portion of the anchor is engageable with a papillary muscle or a heart wall when the anchor is in the deployed configuration; and
the body portion of the anchor is configured to be coupled with an anchoring filament.

9. The device of claim 8, wherein the tissue-engaging portion of the anchor comprises a plurality of arms coupled to the body portion, at least one arm of the plurality of arms having a proximal end coupled to the body portion, a distal end extending away from the proximal end of the arm, and a central portion between the proximal end and the distal end of the arm, the at least one arm being movable between a first elongated configuration and a second bowed configuration with the central portion of the arm extending radially away from the body portion of the anchor a greater distance than the distance between the distal end of the at least one of the plurality arms and the body portion of the anchor when the anchor moves from the delivery configuration to the deployed configuration.

10. The device of claim 9, wherein all of the plurality of arms are movable between the first elongated configuration and the second bowed configuration.

11. The device of claim 8, wherein the anchor is movable between the delivery configuration and the deployed configuration as the anchor is expelled from a distal end of the delivery catheter.

12. The anchor of claim 10, wherein each of the plurality of arms has a distal tip extending axially toward the body portion and pointing radially away from the body portion of the anchor when the arms are in the second bowed configuration.

13. The system of claim 8, wherein:
the tissue-engaging portion of the anchor comprises a plurality of arms coupled to the body portion of the anchor; and
the plurality of arms cross each other as they move from the first configuration to the second configuration.

14. A method of anchoring an artificial chordae tendineae to a papillary muscle or heart wall, the method comprising:
inserting a catheter through a heart valve, the catheter containing an anchor having a body portion coupled to an artificial chordae tendineae;
positioning the catheter adjacent to a targeted papillary muscle or heart wall;
moving the anchor out of the catheter so that the anchor moves from a delivery configuration to a deployed configuration, wherein when the anchor is in the delivery configuration the anchor has a first outer dimension and when the anchor is in the deployed configuration the anchor has a second outer dimension, the first outer dimension being smaller than the second outer dimension;
engaging the tissue-engaging portion of the anchor with the targeted papillary muscle or heart wall when the anchor is moved to the deployed configuration; and
extending the artificial chordae tendineae from the body portion of the anchor to a heart leaflet;
wherein:
in the delivery configuration, the tissue-engaging portion of the anchor includes a plurality of elongated arms extending distally away from the body portion with distal tips thereof directed radially-inwardly toward the body portion such that the distal tips do not contact the catheter; and
in the deployed configuration each of the elongated arms of the anchor has a central portion extending radially away from the body portion of the anchor, a distal end extending radially toward the body portion of the anchor and axially toward the body portion of the anchor, and a distal tip extending axially toward the body portion of the anchor and radially away from the body portion of the anchor.

15. The method of claim 14, further comprising visualizing, using a medical visualization technique, the position of the anchor with respect to the targeted papillary muscle or heart wall before moving the anchor out of the catheter.

16. The method of claim 14, wherein when the arm of the anchor moves from the first position to the second position a tip of the arm pierces the targeted papillary muscle or heart wall and then extends away from the body portion of the anchor.

* * * * *